United States Patent
Eastwood et al.

(10) Patent No.: US 9,561,300 B2
(45) Date of Patent: Feb. 7, 2017

(54) HEMOSTATIC COMPOSITIONS AND DRESSINGS FOR BLEEDING

(75) Inventors: Linda Eastwood, Beverly Hills, CA (US); Harold Coons, Beverly Hills, CA (US); James M. Sinclair, Beverly Hills, CA (US); Matthew D. Bacchetta, New York, NY (US); Gopal Singh, New York, NY (US)

(73) Assignees: YES, INC., Beverly Hills, CA (US); THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 107 days.

(21) Appl. No.: 14/344,998

(22) PCT Filed: Sep. 14, 2012

(86) PCT No.: PCT/US2012/055518
§ 371 (c)(1),
(2), (4) Date: Apr. 6, 2015

(87) PCT Pub. No.: WO2013/048787
PCT Pub. Date: Apr. 4, 2013

(65) Prior Publication Data
US 2015/0283286 A1    Oct. 8, 2015

Related U.S. Application Data

(60) Provisional application No. 61/539,353, filed on Sep. 26, 2011.

(51) Int. Cl.
*A61L 15/40*    (2006.01)
*A61L 15/38*    (2006.01)
(Continued)

(52) U.S. Cl.
CPC .............. *A61L 15/38* (2013.01); *A61K 31/185* (2013.01); *A61K 31/722* (2013.01); *A61K 33/06* (2013.01);
(Continued)

(58) Field of Classification Search
CPC .......... A61L 15/40; A61L 15/18; A61L 15/28; A61L 15/32
See application file for complete search history.

(56) References Cited

U.S. PATENT DOCUMENTS

| 4,393,048 A | 7/1983 | Mason, Jr. et al. |
| 4,453,939 A | 6/1984 | Zimmerman et al. |

(Continued)

FOREIGN PATENT DOCUMENTS

| RU | 2040252 C1 | 7/1995 |
| RU | 2063246 C1 | 7/1996 |

(Continued)

OTHER PUBLICATIONS

Written Opinion for PCT/US2012/055518, 3 pages (Jan. 11, 2013).
(Continued)

*Primary Examiner* — Rosanne Kosson
(74) *Attorney, Agent, or Firm* — Choate, Hall & Stewart, LLP (57) ABSTRACT

The present invention provides hemostatic compositions comprising components of the flowers of pharmaceutical chamomile (*Chamomilla recutita*), the leaves of dioecious nettle (*Urtica dioica*), kaolin, chitosan, fibrinogen and thrombin. Further inclusion of a biocompatible polymeric base, particularly an alignate, generates a composition with superior and broad spectrum hemostatic capabilities, including the ability to arrest arterial hemorrhage. The invention further provides methods of using the inventive compositions in to reduce or stop bleeding, as well as a variety of
(Continued)

apparatuses useful in hemostatic contexts that incorporate the inventive compositions. In one particular embodiment, the invention provides hemostatic dressings in which a polymeric layer incorporating chamomile, nettle, kaolin, chitosan, fibrinogen and thrombin components is applied to a textile or fabric material, for example a non-woven viscose.

25 Claims, 3 Drawing Sheets (51) Int. Cl.
| | | |
|---|---|---|
| A61L 15/44 | (2006.01) | |
| A61K 31/722 | (2006.01) | |
| A61K 36/185 | (2006.01) | |
| A61K 36/28 | (2006.01) | |
| A61K 45/06 | (2006.01) | |
| A61K 38/48 | (2006.01) | |
| A61K 31/185 | (2006.01) | |
| A61K 33/06 | (2006.01) | |
| A61L 15/18 | (2006.01) | |
| A61L 15/22 | (2006.01) | |
| A61K 38/36 | (2006.01) | |
| A61L 15/28 | (2006.01) | |
| A61L 15/32 | (2006.01) | |

(52) U.S. Cl.
CPC ............ *A61K 36/185* (2013.01); *A61K 36/28* (2013.01); *A61K 38/363* (2013.01); *A61K 38/4833* (2013.01); *A61K 45/06* (2013.01); *A61L 15/18* (2013.01); *A61L 15/225* (2013.01); *A61L 15/28* (2013.01); *A61L 15/32* (2013.01); *A61L 15/40* (2013.01); *A61L 15/44* (2013.01); *A61L 2400/04* (2013.01); *C12Y 304/21005* (2013.01)

(56) References Cited

U.S. PATENT DOCUMENTS

| | | | |
|---|---|---|---|
| 4,616,644 | A | 10/1986 | Saferstein et al. |
| 4,658,839 | A | 4/1987 | Dallal et al. |
| 4,673,568 | A | 6/1987 | Grollier et al. |
| 5,192,689 | A | 3/1993 | Hemker et al. |
| 5,773,033 | A | 6/1998 | Cochrum et al. |
| 5,800,372 | A | 9/1998 | Bell et al. |
| 6,124,273 | A | 9/2000 | Drohan et al. |
| 6,320,029 | B1 | 11/2001 | Miekka et al. |
| 6,638,296 | B2 | 10/2003 | Levinson |
| 6,897,348 | B2 | 5/2005 | Malik |
| 7,094,428 | B2 | 8/2006 | Spillert et al. |
| 7,604,819 | B2 | 10/2009 | Huey et al. |
| 7,968,114 | B2 | 6/2011 | Huey et al. |
| 2003/0129183 | A1 | 7/2003 | Spillert et al. |
| 2004/0237970 | A1 | 12/2004 | Vournakis et al. |
| 2005/0123588 | A1 | 6/2005 | Zhu et al. |
| 2006/0127437 | A1 | 6/2006 | Kennedy et al. |
| 2006/0155235 | A1 | 7/2006 | Sawyer |
| 2007/0190110 | A1 | 8/2007 | Pameijer et al. |
| 2008/0031934 | A1 | 2/2008 | MacPhee et al. |
| 2008/0033331 | A1 | 2/2008 | MacPhee et al. |
| 2008/0033332 | A1 | 2/2008 | MacPhee et al. |
| 2008/0033333 | A1 | 2/2008 | MacPhee et al. |
| 2008/0097271 | A1 | 4/2008 | Lo et al. |
| 2008/0107708 | A1 | 5/2008 | Ng et al. |
| 2008/0139988 | A1 | 6/2008 | Dayan et al. |
| 2008/0145455 | A1 | 6/2008 | Bedard |
| 2008/0171074 | A1 | 7/2008 | Oltarzhevskaya et al. |
| 2008/0317831 | A1 | 12/2008 | Lo |
| 2008/0319476 | A1 | 12/2008 | Ward et al. |
| 2009/0075891 | A1 | 3/2009 | MacPhee et al. |
| 2009/0155342 | A1 | 6/2009 | Diegelmann et al. |
| 2010/0021528 | A1 | 1/2010 | Sackinger et al. |
| 2010/0172958 | A1 | 7/2010 | Lucchesi et al. |
| 2010/0292624 | A1 | 11/2010 | Diegelmann et al. |
| 2010/0324058 | A1 | 12/2010 | Sinauridze et al. |
| 2011/0021964 | A1 | 1/2011 | Larsen et al. |
| 2011/0064785 | A1 | 3/2011 | Daniels et al. |
| 2014/0220103 | A1 | 8/2014 | Bacchetta et al. |

FOREIGN PATENT DOCUMENTS

| | | |
|---|---|---|
| RU | 2101033 C1 | 1/1998 |
| RU | 2157243 C1 | 10/2000 |
| RU | 2179428 C2 | 2/2002 |
| RU | 2193897 C2 | 12/2002 |
| WO | WO-97/28832 A1 | 8/1997 |
| WO | WO-99/59647 A1 | 11/1999 |
| WO | WO-2006/067549 A1 | 6/2006 |
| WO | WO-2007/009050 A2 | 1/2007 |
| WO | WO-2010/031995 A2 | 3/2010 |
| WO | WO-2013/048787 A1 | 4/2013 |

OTHER PUBLICATIONS

Chou et al., Chitosan enhances platelet adhesion and aggregation, Biochem. Biophys. Res. Commun., Abstract only, 302(3):480-483 (2003).

Fenton et al., Human Thrombins, Production, Evaluation, and Properties of Alpha-Thrombin, J. Biol. Chem., 252(11):3587-3598 (1977).

Holcomb et al., Effect of dry fibrin sealant dressings versus gauze packing on blood loss in grade V liever injuries in resuscitated swine, J. Trauma, Abstract only, 46(1):49-57 (1999).

International Preliminary Report on Patentability for PCT/IB2004/004355, issued on Jun. 26, 2007.

International Preliminary Report on Patentability for PCT/US2012/055518, issued on Apr. 1, 2014.

International Search Report for PCT/IB2004/004355, mailed Sep. 15, 2005.

International Search Report for PCT/US2012/055518, mailed Jan. 11, 2013.

Iso et al., Solution properties of Sodium alginate from brown seaweeds living along the coast of Japan—II Algini Acid Contents, Bull. Jap. Soc. Scientific Fisheries, 44(12):1375-1379 (1978).

Milstone, H., Purification of Thrombin, J. Gen. Physiol., 25(5):679-687 (1942).

Moore et al., Organ injury scaling, Surg. Clin. North Am., 75(2):293-303 (1995).

Schreiber et al., The effect of recombinant factor VIIa on noncoagulopathic pigs with grade V liver injuries, J. Am. Coll.. Surgery, Abstract only, 196(5):691-697 (2003).

Sodium Alginate Powder website (<http://www.clubnatural.com/alginate.html>) accessed Jul. 20, 2010.

Soni et al., Evaluation of the health aspects of methyl paraben: a review of the published literature, Food Chem. Toxicol., 40(10):1335-1373 (2002).

Daum, P. et al., Fibrinogen in Plasma by Rate of Clot Formation on the STA—Compact, 2001-2002.

HEMOSTATIC COMPOSITIONS AND DRESSINGS FOR BLEEDING

CROSS REFERENCE TO RELATED APPLICATIONS

This application is a U.S. national phase application under 35 U.S.C. 371 of international PCT application no. PCT/US2012/055518, filed Sep. 14, 2012, which claims priority to and benefit of U.S. Provisional Patent Application No. 61/539,353, filed Sep. 26, 2011. The entire contents of these applications are hereby incorporated by reference.

BACKGROUND

The blood coagulation cascade is an exquisite example of a responsive self-assembly process. When a wound if formed, a cascade of events is initiated. The net result of the cascade is an assembly of the globular protein fibrinogen, which is catalyzed by a second protein, thrombin, to yield chains of fibrin. A network of insoluble fibrin chains forms the hemostatic "plug" or clot, which presents a physical barrier to the loss of blood from the wound.

The coagulation cascade is a delicately balanced series of events; if it occurs too easily, blood clots may form in unwanted areas, leading to strokes or other complications. It is, however, possible to harness the clotting power of fibrin to create haemostatic dressing or bandages. There is a vital need for haemostatic dressings that can staunch the bleeding from serious trauma.

A wide variety of compositions and devices have been developed for use in controlling bleeding. However, available compositions and dressings typically have only a modest hemostatic effect, so that bleeding continues for several (e.g., 2-3 minutes or more) after application of composition or dressing. Additionally, many dressings have only modest antiseptic abilities. Also, typical dressings are prepared from materials that have a tendency to adhere to the injured surface, causing significant pain to the patient when the dressing is applied or removed. Because of the modest hemostatic and/or antiseptic activity, standard dressings often need to be changed frequently, further exacerbating adhesion problems.

Massive hemorrhaging, and particularly arterial bleeding, from severe trauma remains extremely difficult to control and treat. Advanced wound dressing are frequently employed in battlefield and emergency situations, but the results have been mixed. The HemCon® bandage, made from a chitosan derived from shrimp shells, was approved by the Pentagon's advisory committee on combat medicine in 2003 as the preferred dressing for combat. However, animal studies have shown that HemCon® is no more effective than gauze, and in certain circumstances even less effective. The bandage also proved less than effective in battlefield situations where it proved too small and rigid for battlefield injuries, rendering it extremely difficult to use on extremities.

Another advanced battlefield wound dressing, WoundStat®, has also proven inadequate, and has further been linked with potentially deadly complications in animal studies. The bandages are comprised in part of clay-like kaolin, which has been hypothesized to facilitate coagulation and clotting. However, in the particular WoundStat formulation, the kaolin can break loose and drift into veins and arteries, potentially causing deadly clots intraarterial and intravascular clots.

SUMMARY OF THE INVENTION

There remains a need for the development of improved hemostatic compositions, methods, and devices. The ideal hemostatic dressing will require little training; be nonperishable, durable, flexible and inexpensive; adhere to the wound only; pose no direct risk of disease; not induce a tissue reaction; and effectively control hemorrhage from arterial, venous and soft tissue bleeding. Embodiments of the invention achieve these goals and more. They demonstrate remarkable and unexpected hemostasis achieved by particular chamomile/nettle compositions in combination with kaolin, chitosan, fibrinogen, and thrombin components. Individual components of inventive compositions have been reported to have some hemostatic and/or antiseptic activity. For example, kaolin has been known for decades to activate blood clotting. It is a naturally occurring layered silicate mineral having alternating tetrahedral sheets and octahedral sheets of alumina octahedra linked via the oxygen atoms of hydroxyl groups, which comprises about 50% alumina, about 50% silica, and trace impurities. Likewise, chitosan—a linear polysaccharide composed of randomly distributed β-(1-4)-linked D-glucosamine (deacetylated unit) and N-acetyl-D-glucosamine (acetylated unit)—is known to facilitate rapid blood clotting, and has recently gained approval in the United States and Europe for use in bandages and other hemostatic agents. Chitosan hemostatic products have been shown to reduce blood loss in comparison to gauze dressings and increase patient survival (Pusateri, et al., "Effect of a chitosan-based hemostatic dressing on blood loss and survival in a model of severe venous hemorrhage and hepatic injury in swine", 2003 J. Trauma 4 (1): 177-182).

There are numerous agents reported in the literature that are said to show such hemostatic and/or antiseptic activities. However, there remains a need for haemostatic compositions and wound dressings comprising such compositions that greatly reduce clotting time, reduce blood loss, and improve chances of patient survival. It has yet to be reported how known hemostatic agents such as kaolin and chitosan can be combined to achieve results greater than either of the components individually. Embodiments of the present invention are based on the surprising discovery that certain compositions comprised of chamomile and nettle components in combination with kaolin, chitosan, fibrinogen and thrombin synergistically reduce clotting time to a far greater extent than any of the components individually and/or than other combinations. Moreover, compositions of the invention achieve such results without loss of antiseptic properties, for example those imparted by the chamomile components.

In some embodiments, the present invention provides compositions comprising chamomile, dioecious nettle, kaolin, chitosan, fibrinogen, thrombin components and a biocompatible polymer. In some embodiments, the present invention provides dressings, such as bandages. In some embodiments, the chamomile and dioecious nettle components are present at a weight ratio relative to the biocompatible polymer of 0.3-0.9:1.

In other embodiments of the compositions of the invention, the kaolin, chitosan, fibrinogen and thrombin components are present at a total weight ratio of 0.2-0.8:1 by weight of the biocompatible polymer. In still yet other embodiments, the kaolin, chitosan, fibrinogen and thrombin components are present at a total weight ratio of 0.2-1.4:1 by weight of the biocompatible polymer. In a particular embodiment, the kaolin:biocompatible polymer ratio by weight is 0.01-0.03:1, the chitosan:biocompatible polymer ratio by weight is 0.02-0.07:1, the fibrinogen:biocompatible polymer ratio by weight is 0.30-1.2:1, and the thrombin:biocompatible polymer ratio by weight is 0.03-0.08:1. In still yet other embodiments, the chamomile and dioecious nettle components are present at a weight ratio relative to the biocompatible polymer of 0.3-0.9:1, the kaolin:biocompatible polymer ratio by weight is 0.01-0.03:1, the chitosan:biocompatible polymer ratio by weight is 0.02-0.07:1, the fibrinogen:biocompatible polymer ratio by weight is 0.30-1.2:1, and the thrombin:biocompatible polymer ratio by weight is 0.03-0.08:1.

In some embodiments of the composition of the invention, the chamomile and nettle components are present at an amount within a weight ratio range of about 0.3-0.9:1 relative to the amount by weight of biocompatible polymer, kaolin is present in a total amount of about 1 to 5 grams, chitosan is present in a total amount of about 4-10 grams, fibrinogen is present in a total amount of about 10 to 20 grams, and thrombin is present at a level of about 100 to 200 kilo units. In other embodiments, the chamomile and nettle components are present at an amount within a weight ratio range of about 0.3-0.9:1 relative to the amount by weight of biocompatible polymer, chitosan is present in a total amount of about 4 grams, kaolin is present at a total amount of about 1 gram, fibrinogen is present at a total amount of about 20 grams, and thrombin is present at a level of 150 kilo units.

In particular embodiments, the biocompatible polymer is selected from one or more of agarose, agar, carrageen, alginic acid, alginate, an alginic acid derivative, a hyaluronate derivative, a polyanionic polysaccharide, chitin, chitosan, fibrin, a polyglycolide, a polylactide, a polycaprolactone, a dextran or copolymer thereof, polyvinyl pyrrolidone, a polyacrylate, a wax, a polyethylene-polyoxypropylene-block polymer, wool fat, poly(L-lactic acid), poly(DL-Lactic acid) copoly(lactic/glycolic acid), cellulose, a cellulose derivative, a glycol, polylactide-polyglycolide, polymethyldisiloxane, polycaprolactone, polylactic acid, and ethylene vinyl acetate. In some embodiments, the biocompatible polymer comprises a hydrophilic polymer. In yet other embodiments, the biocompatible polymer comprises alginic acid, alginate or other alginic acid derivative. In other embodiments, the biocompatible polymer comprises a hydrogel.

In some embodiments of the invention, the compositions further comprise an additional therapeutic agent. In particular embodiments, the additional therapeutic agent is selected from one or more of an antimicrobial, an antibiotic, an antimyobacterial, an antifungal, an antiviral, a neoplastic agent, an agent affecting the immune response, an antithrombotic, an antihyperlipidemic agent, a cardiac drug, a thyromimetic or antithyroid drug, an adrenergic, an antihypertensive agent, a cholinergic, an anticholinergic, an antispasmodic, an antiulcer agent, a skeletal and/or smooth muscle relaxant, a prostaglandin, a general inhibitor of the allergic response, an antihistamine, a local anesthetic, an analgesic, a narcotic antagonist, an antitussive, a non-steroidal anti-inflammatory agent, a steroidal anti-inflammatory agent, an antioxidant, a vaso-active agent, a bone-active agent, an antiarthritic, a vitamin, or a diagnostic agent. In other embodiments, the additional therapeutic agent is selected from one or more of an antimicrobial, an antibiotic, an antimyobacterial, an antifungal, an antiviral, a local anesthetic, an analgesic, an antioxidant, or a vitamin.

In some embodiments, the present invention provides a dressing for topical or transdermal administration comprising embodiments of the compositions of the invention. In particular embodiments, the dressing comprises a textile material and the composition is applied on one surface of the textile material. In some embodiments, the textile material comprises a non-woven material. In some embodiments, the textile material has been stitched with reinforced threads. In particular embodiments, the rows of stitching are separated from one another by a distance within the range of 1.0-10.0 mm. In certain embodiments, the textile material is a 6×10 cm pad or a 10×18 cm pad.

In some embodiments, the present invention provides methods of controlling or lessening the severity of bleeding in a patient in need thereof, wherein said method comprises administering to said patient compositions according to embodiments of the invention. In some embodiments, the present invention provides methods of controlling or lessening the severity of bleeding in a patient in need thereof, wherein said method comprises the application of the dressing according to embodiments of the invention. Certain methods provided by the present invention further comprise the application of external pressure. In particular embodiments, the bleeding is associated with a wound, accidental injury, a dental procedure, or a surgical procedure. In particular embodiments, the bleeding is arterial bleeding.

In some embodiments, the present invention provides methods of promoting wound healing in a patient in need thereof, wherein said method comprises applying compositions of the invention to a wound on the patient. In still other embodiments, the present invention provides a method of treating a burn in a patient in need thereof, wherein said method comprises applying a composition of the invention to a burn on the patient.

Embodiments of the invention are particularly useful for the treatment of uncontrolled hemorrhage, the most common cause of death on military battlefields and the second leading cause of death in civilian trauma centers. It has been unexpectedly discovered that hemostatic compositions according to the invention possess the capability to induce clotting of even rapid arterial bleeding. Embodiments of the invention may be applied to a hemorrhaging wound at or nearby the geographical location where the trauma was incurred; thereby permitting treatment of the hemorrhage within minutes or even seconds. The prompt, efficient, and synergistic treatment of a hemorrhage facilitated by embodiments of invention can reduce morbidity and mortality through early reduction or elimination of blood loss. Prevention of significant blood loss reduces or eliminates hypothermia, coagulopathy, acidosis, and late "second-hit" mortality that occurs through the development of sepsis and multiple organ failure. Prevention of significant blood loss also facilitates quick evacuation to a trauma center where the extent of injuries can be evaluated and treated. It also reduces the need for blood transfusions, which itself correlates with increased mortality independent of the amount or severity of blood loss. Embodiments of the invention are also highly advantageous in a hospital setting where they may be used to prevent or arrest hemorrhaging after surgery.

The invention further provides methods of using inventive compositions to reduce or stop bleeding and/or to treat wounds or burns, as well as a variety of apparatuses useful in hemostatic contexts that incorporate inventive compositions. In one particular embodiment, the invention provides hemostatic dressings. This embodiment is exemplified herein with a bandage comprising chamomile and nettle components into which kaolin, chitosan, fibrinogen, and thrombin are combined via lyophilization.

DETAILED DESCRIPTION OF CERTAIN EMBODIMENTS

Hemostatic Compositions

As described above, the present invention provides hemostatic compositions containing specified amounts of chamomile and nettle components, and further comprising kaolin, chitosan, fibrinogen, and thrombin. In some embodiments, the compositions contain a biocompatible polymer or gel, e.g., an alginate. Alternatively or additionally, inventive hemostatic compositions may contain other pharmaceutical agents.

Chamomile and Nettle

The present invention provides hemostatic compositions containing chamomile and nettle components. Hemostatic compositions containing chamomile and nettle components are known in the art.

In some embodiments, the inventive compositions contain chamomile components and nettle components in a ratio within the range of about 0.2-5.0:1.0 by weight of chamomile flowers to nettle leaves. In some embodiments, this ratio is within the range of about 1.0-3.0 chamomile flowers to nettle leaves.

As described in Example 1, for example, chamomile and nettle components may be provided as an extract of chamomile and nettle plants. In some embodiments, a chamomile extract is prepared from chamomile flowers; in some embodiments, a nettle extract is prepared from nettle leaves. Chamomile and nettle extracts may be prepared separately and then combined, or alternatively chamomile and nettle plant portions may first be combined together (before or after grinding), so that a single extract is prepared from the combination.

Example 1 describes preparation of an aqueous extract of chamomile flowers and nettle leaves. Those of ordinary skill in the art will readily appreciate that alternative extraction strategies (e.g., alcohol extraction) may alternatively be employed, so long as appropriate chamomile and nettle active components are obtained. Similarly, those of ordinary skill in the art will appreciate that appropriate chamomile and nettle components may be provided by techniques other than extraction; indeed, in some cases it may be possible to obtain isolated components from commercial sources.

However the chamomile and nettle components are obtained, they are desirably combined in amounts appropriately based on the above-noted weight ratios for chamomile flowers and nettle leaves. For example, if individual isolated components (e.g., discrete chemical compounds) or other component preparations are obtained, they are desirably combined with one another to achieve individual component amounts that would be present had chamomile flowers and nettle leaves been mixed at the indicated weight ratios, as described above and in Example 1.

Chamomile flowers (fresh or dried), water, and oil can be obtained from any of a variety of commercial sources (e.g., Artemis herbs), or can be prepared according to known techniques. The flowers of chamomile contain about 1-2% volatile oils including alpha-bisabolol, alpha-bisabolol oxides A & B, and matricin (usually converted to chamazulene during hot water extraction or steam distillation). Other components include the flavonoids apigenin, luteolin, and quercetin. Bitter glycosides (anthemic acid), coumarins (including umbelliferon and herniarin), phenolic carboxylic acids, polysaccharides, mucilage, choline, amino acids, tannins, and malic acid.

Nettle plants or leaves can be obtained fresh or dried from a variety of commercial sources, as can various extracts. Techniques for cultivating and processing nettle are also well known in the art. Nettle is known to contain amines, including histamine, formic acid, serotonin, flavonoids (including rutin and quercitrin), glycocides, tannins, carotenes, and vitamin C, among other components.

In particular embodiments of the invention, the chamomile and nettle components are combined or integrated with a biocompatible polymer. The chamomile/nettle/biocompatible polymer combination may be formed or integrated into a fibrous and/or absorbent material such as a bandage or wound dressing. In such embodiments, the chamomile/nettle/biocompatible polymer components form a base product into which additional component may be added as described below. However, embodiments of the invention are not limited by the order of addition of the various components. Those of skill in the art can readily appreciate that in additional embodiments other components (e.g., kaolin or chitosan) may be integrated into a base support and the chamomile/nettle components added subsequently. Nonetheless, in certain embodiments the chitosan and kaolin are applied first to maximize their absorbency, and the fibrinogen and thrombin are applied subsequently to facilitate contact with the bleeding surface.

Kaolin

There are many plasma factors (proteins) that play integral roles in the coagulation cascade. These factors include proaccelerin (Factor V), proconverin (Factor VII), antihemophilic globulin (VIII), Christmas Factor (Factor IX), Stuart-Prower Factor (Factor X), plasma thromboplastin antecedent (Factor XI), Hageman factor (Factor XII), and fibrin stabilizing factor (Factor XIII). Different enzymes act upon these factors during specific junctions of the coagulation cascade to initiate, build and stabilize a blood clot.

Kaolin initiates coagulation processes by contact with Factor XII. This interaction leads to the transformation of Factor XII, Factor XI and prekallikrein to their activated forms. The activation of Factor XII to Factor XIIa is highly dependent on the presence of HMK and kaolin since both these compounds increase the susceptibility of Factor XII to plasma kallikrein. Although Factor XII can activate prekallikrein without kaolin, kaolin's presence markedly enhances the rate of activation. Kaolin-based hemostatic agents and material incorporating such agents have been described previously; for example, in U.S. Pat. No. 7,604, 819, herein incorporated by reference.

In the present invention, a kaolin solution may be prepared, for example, by dissolving approximately 5-15 grams of kaolin in a suitable volume of phosphate buffered saline ("PBS") or other solvent. The solution may be mixed at room temperature or heated. In particular embodiments of the invention, approximately 1-10 grams of kaolin may be applied per bandage, either before or after the addition of chamomile/nettle components.

Chitosan

Chitosan acts to promote coagulation by influencing platelet aggregation via its mucoadhesive properties. For example, it has been shown that that after initial (5 min) and long-term (30 min) contact of platelets with chitosan, the platelet adhesion to chitosan-coated microtiter plates was dose-dependently increased compared to that of solvent control. Chou, T. C. et al, *Biochem Biophys Res Commun.* 2003 Mar. 14; 302(3):480-3. It has been postulated that the mechanisms of action of chitosan may be associated, at least partly, with the ability to mobilize calcium ions. Calcium ions are essential for clotting as they are necessary for the formation of active thromboplastin and for the conversion of prothrombin to thrombin. Chitosan-based wound dressings are known in the art, as are methods of purifying and preparing chitosan for use hemostatic uses; for example, U.S. Pat. No. 5,773,033.

In the present invention, chitosan may be prepared, for example, by dissolving 5-15 grams is a suitable volume of PBS or other solvent. In order to facilitate chitosan entering into solution, the solution may be made acidic and heated during mixing. After a suitable time period, the solution may be made slightly basic. After cooling, approximately 2-20 grams may be applied to a bandage (e.g., a chamomile/nettle bandage as particularly described herein).

Fibrinogen

Fibrinogen is a known component of the coagulation cascade. Along with prothrombin, it is one of two major plasma proteins involved in blood clotting. The enzymatic conversion by thrombin of the soluble protein fibrinogen into the insoluble protein fibrin is an essential step in blood coagulation. Fibrinogen is readily precipitated from the plasma of circulating blood, and uses in hemostatic compositions are known in the art (see U.S. Pat. No. 5,773,033, incorporated by reference herein).

Fibrinogen used according to embodiments of the invention may be prepard from plasma isolated from human blood or the blood of any other animal. The isolated fibrinogen is then purified to remove other plasma proteins. The fibrinogen may be isolated from a subject's own blood prior or may be derived from plasma obtained from blood other than that of the subject (e.g., from a blood bank). During a typical isolation process, fibrinogen is prepared from whole blood by separating red blood cells from plasma. The whole blood may be drawn from a subject directly into a buffered anticoagulant agent, such as sodium citrate. The platelets and plasma may then be separated from the red blood cells by centrifugation. The plasma may then be removed and centrifuged a second time at high speed to separate the platelets from the plasma. Ammonium sulfate may then be used for the precipitation, isolation and purification of the fibrinogen as known in the art.

Suitable fibrinogen formulations are also commercially available. Fibrinogen can also be obtained from the supernatants or paste of recombinant tissue cultures, yeast, bacteria or any host cell capable of expressing human or mammalian plasma protein introduced through standard recombinant DNA and molecular biology techniques. Fibrinogen used in compositions of the invention is of appropriate purity known to those of skill in the art, and can be subjected to multiple chromatographic purification techniques (e.g., affinity chromatography, immunoaffinity chromatography, size-exclusion chromatography, etc.) to remove substances that may cause degradation of any components of the inventive composition during storage or use.

The fibrinogen used in compositions of the invention can be a fibrinogen complex or any fibrinogen, or a derivative or metabolite thereof. Constituents of a fibrin complex can include albumin, plasminogen, Factor XIII and polysorbate 80. Approximately 5-15 grams of fibrinogen are used (e.g., are applied to a bandage and particularly to a chamomile/nettle bandage as described herein) in particular compositions of the invention.

Thrombin

Thrombin is a serine protease of primary importance to the coagulation cascade. It causes clotting by converting fibrinogen to fibrin. Thrombin catalyzes the hydrolysis of arginine-glycine peptide bonds in fibrinogen, thereby generating fibrin monomers. The fibrin monomers (elastic, thread-like insoluble protein monomers) spontaneously associate in a staggered array to form an insoluble fibrin clot. Generally, the more thrombin present during coagulation, the faster clotting proceeds.

Thrombin is formed from prothrombin, an inactivate circulating precursor. The conversion of thrombin to prothrombin occurs during tissue injury, bleeding or blood loss, and the activation of prothrombin depends on the presence of calcium ions and thromboplastins released or derived from damaged tissues.

Thrombin can be obtained from human or mammalian plasma by any isolation and purification methods known to those of skill in the art. For example, one exemplary method is described by Milstone, *J Gen Physiol.* 1942 May 20; 25(5): 679-687. Suitable thrombin formulations are also commercially available. Thrombin can be obtained from the supernatants or paste of recombinant tissue cultures, yeast, bacteria or any host cell capable of expressing human or mammalian plasma protein introduced through standard recombinant DNA and molecular biology techniques. In particular embodiments, human thrombin is prepared from Fraction III paste as described (Fenton, et al, J. Biol. Chem. 1977 252:3587-98). Thrombin used in compositions of the invention is of appropriate purity known to those of skill in the art, and can be subjected to multiple chromatographic purification techniques (e.g., affinity chromatography, immunoaffinity chromatography, size-exclusion chromatography, etc.) to remove substances that may cause degradation of any components of the inventive composition during storage or use.

Approximately 50-150 kilo units of thrombin are used (e.g., are applied to a bandage and particularly to a chamomile/nettle bandage as described herein) in particular embodiments of the invention.

Biocompatible Polymer or Gel

Inventive compositions may optionally include one or more additional components. In many instances, it will be desirable to include a biocompatible polymer or gel, for example to localize and impart a useful consistency to the composition. A variety of biocompatible polymers are known in the art.

In certain embodiments, the biocompatible polymer comprises agarose, agar, carrageen, alginic acid, alginate and/or other alginic acid derivatives, hyaluronic acid and/or hyaluronate derivatives, polyanionic polysaccharides, chitin, chitosan, fibrin, polyglycolide, polylactide, polycaprolactone, dextran and/or copolymers thereof, polyvinyl pyrrolidone, polyacrylates, waxes, polyethylene-polyoxypropylene-block polymers, wool fat, poly(L-lactic acid), poly(DL-Lactic acid) copoly(lactic/glycolic acid), cellulose and/or its derivatives such as sodium carboxymethyl cellulose, ethyl cellulose and/or cellulose acetate, glycols such as propylene glycol or polyethylene glycol, polylactide-polyglycolide, polymethyldisiloxane, polycaprolactone, polylactic acid, ethylene vinyl acetate, or combinations thereof.

In some embodiments, the biocompatible polymer comprises a hydrophilic polymer. Useful hydrophilic polymers include, for example, hydrophilic diols, hydrophilic diamines, and combinations thereof. Hydrophilic diols can be, for example, poly(alkylene)glycols, polyester-based polyols, polycarbonate polyols, or combinations thereof. As used herein, the term "poly(alkylene)glycol" refers to polymers of lower alkylene glycols such as poly(ethylene)glycol, poly(propylene)glycol polytetramethylene ether glycol (PTMEG), and combinations thereof Biocompatible polymers for use in accordance with the present invention may be or include a hydrogel, such as, for example, a copolymer or block-polymer or the like. Useful hydrogels include crosslinked keratin, polymethylmethacrylate, polyethylene glycol, polyalkoxyalkyl (meth)acrylate, ethylene/vinylalcohol copolymer, polyurea, a polyurethane polyurethane/polyurea, and combinations thereof, to name but a few.

In addition to providing useful localization and retention attributes to the inventive hemostatic compositions, polymers or gels that attract, absorb, or otherwise incorporate water may have additional advantages, including, for example, an ability to promote coagulation. To give but one example, alginate can enhance the hemostatic properties of compositions according to the present invention.

The amount of biocompatible polymer or gel utilized in accordance with the present invention will be selected to permit or achieve the desired hemostatic results. In some embodiments, chamomile/nettle components will be present at an amount within a weight ratio range of about 0.3 to 0.9 of the amount by weight of biocompatible polymer or gel (i.e., 0.3-0.9:1). In some embodiments, the ratio amount will be within a range of about 0.4 to 0.6 by weight of the biocompatible polymer or gel (i.e., 0.4-0.6:1); in some embodiments the amount will be within a range of about 0.5-0.55 (i.e., 0.5-0.55:1). Some embodiments contain 0.33-0.92 chamomile/nettle components by weight ratio to an alginate composition; others contain 0.5-0.55 chamomile/nettle components by weight in alginate. This weight relationship makes it possible to effectively increase the coagulability of blood, preserve high antiseptic and anti-inflammatory properties, and, at the same time, maintain sufficient viscosity in the wound to facilitate clotting, which, in the final analysis, influences the speed with which bleeding is halted.

In some embodiments, the kaolin/chitosan/fibrinogen/thrombin components will be present at an amount within a weight ratio range of about 0.30 to 0.50 of the amount by weight of the biocompatible polymer or gel. In some embodiments, the amount will be within a weight ratio range of about 0.2 to 0.8 by weight of the biocompatible polymer or gel; in some embodiments the amount will be within a range of about 0.2-1.4 of the biocompatible polymer or gel. In particular embodiments, the kaolin/chitosan/fibrinogen/thrombin components may be present individually at an amount within the following weight ratio ranges relative to the amount by weight of the biocompatible polymer or gel: kaolin—about 0.01 to 0.03 by weight of biocompatible polymer or gel; chitosan—about 0.02 to 0.07 by weight of biocompatible polymer or gel; fibrinogen—about 0.30 to 1.2 by weight of biocompatible polymer or gel; and thrombin—about 0.03 to 0.08 by weight of biocompatible polymer or gel. In yet other embodiments, the thrombin component is present at 100-200 kilo units per bandage. As with the chamomile/nettle components, the weight relationship of the kaolin/chitosan/fibrinogen/thrombin makes it possible to effectively increase the coagulability of blood, preserve high antiseptic and anti-inflammatory properties, and, at the same time, maintain sufficient viscosity in the wound to facilitate clotting, which, in the final analysis, influences the speed with which bleeding is halted.

In a particular embodiment, the chamomile/nettle components are present at an amount within a weight ratio range of about 0.3 to 0.9 of the amount by weight of biocompatible polymer or gel, kaolin is present in a total amount of about 1 to 5 grams, chitosan is present in a total amount of about 4-10 grams, fibrinogen is present in a total amount of about 10 to 20 grams, and thrombin is present at a level of about 100 to 200 kilo units. In still yet a more particular embodiment, the chamomile/nettle components are present at an amount within a weight ratio range of about 0.3 to 0.9 of the amount by weight of biocompatible polymer or gel, chitosan is present in a total amount of about 4 grams, kaolin is present at a total amount of about 1 gram, fibrinogen is present at a total amount of about 20 grams, and thrombin is present at a level of 150 kilo units.

It should also be appreciated that the range of components in relation to the biocompatible polymer or gel may ensure sufficient flexibility and absorbency of the final composition. Although increasing the ranges above may increase hemostatic properties, the benefit may be outweighed by the loss of flexibility and absorbency. As noted above, suitable flexibility is critical for ensuring that the compositions of the invention can be applied to the unique geometry of individual subjects and anatomical locations, which permits use in a wide variety of traumatic injuries. Nonetheless, embodiments of the present invention encompass variations within the skill and reasonable experimentation of those in the art to modify the absolute and relative percentage ranges of the components to maximize hemostatic properties, flexibility and absorbency.

Bandages or Dressings

In particular embodiments of the invention, the inventive compositions are incorporated or impregnated into wound dressing or bandages. The dressings can be prepared by any method known to those of skill in the art. The dressings are also typically of a size and shape that can be readily handled yet of sufficient size to cover large wounds. The inventive compositions disclosed herein can be applied to all or part of the area of a dressing.

Many different materials known to those of skill in the art can be employed to form the dressings or bandages. In particular embodiments, the biocompatible polymers and gels described above may be used to form the dressing or bandage. In general, the inventive compositions can be used with any absorbable or semi-absorbable material that is capable of filling a wound or otherwise stemming the flow of blood, yet is pliant enough to effect the application of pressure or other means to fix the material to the wound. The inventive compositions may be incorporated into any number of commercially available dressing types, including: semi-permeable synthetic fabrics, gauze, perforated plastic, polyester fabric, alginates, polyurethane films or foam, hydrocolloid dressings, and cotton. The dressings may be comprised of woven or non-woven fibers.

The inventive compositions can be affixed to the dressings by any means known and available to those skilled in the art. In certain embodiments, the order of addition of the various components described above is not of critical importance. As noted, however, in other embodiments the fibrinogen and thrombin are added only after deposition of the kaolin and chitosan. Those of skill in the art can readily appreciate that the various components can be added sequentially, mixed in combination and subsequently added, or pre-mixed in any combination followed by application of the remaining component. In preferred embodiments, the chamomile/nettle components are mixed with a biocompatible polymer or gel (e.g., alginate) as described above, which is prepared as an aqueous solution. The chamomile/nettle/polymer or gel solution is then layered onto a non-woven textile material comprised of a combination of viscose and cotton fibers stitched with reinforcing thread in rows spaced at suitable intervals. In particular embodiments, the reinforcing threads are spaced at 3-6 mm intervals. Approximately 50-150 grams of the chamomile/nettle/polymer or gel composition are added per square meter of material, and the material is permitted to dry. After drying of the material, the kaolin, chitosan, fibrinogen and thrombin are applied as a lyophilized layer or layers. The lyophilized layers can be applied by any of a variety of techniques, including spraying, sprinkling, electrostatic deposition, or dispensing manifold.

The lyophilization protocol may include pretreatment, freezing, primary drying and secondary drying. Pretreatment includes any method of treating the product prior to freezing; for example, concentrating the product, increasing stability of or adding components, or increasing the surface area thorough milling or particlization. Freezing comprises lowering the kaolin, chitosan, fibrinogen, and thrombin components to a final temperature below the freezing point while under a vacuum. The freezing process optionally includes one or more intervals where the components are held at a specific temperature for a given amount of time. In certain embodiment, the final temperature is between minus 30-80° C.

In particular embodiments of the invention, it is noted that the chamomile/nettle/biopolymer matrix makes the final performance of the new product superior to other commercially available hemostatic compounds. The matrix facilitates presentation of the base chamomile/nettle components, which allows synergistic interactions with the kaolin/chitosan/fibrinogen/thrombin additives to ensure arrest of high pressure arterial bleeding. In such embodiments, the order in which the individual components are added to the matrix is of critical importance. It should be appreciated that, in certain embodiments, it is first necessary to form the chamomile/nettle/biopolymer matrix followed by addition of the remaining components, preferably with the kaolin and chitosan added before addition of fibrinogen and thrombin. Furthermore, it should be noted that, in such embodiments, it is necessary for the additional components (kaolin, chitosan, etc.) to be applied through lyophilization techniques known in the art. Any attempt to apply the additional component in liquid form (e.g., by soaking the chamomile/nettle/biopolymer matrix in buffers of the other components) could leach the chamomile and nettle from the biopolymer, thereby altering the range of chamomile/nettle components relative to the amount by weight of biocompatible polymer or gel. Altering the ratio of the chamomile/nettle components relative to the amount by weight of biocompatible polymer or gel could generate an unfavorable hemostatic profile.

Pharmaceutical Agent

Those of ordinary skill in the art will readily appreciate that it may sometimes be desirable to include one or more additional pharmaceutical agents, in addition to the above-described components, in the hemostatic compositions of the present invention.

For example, composition of the present invention optionally includes one or more of an antimicrobial, an antibiotic, an antimyobacterial, an antifungal, an antiviral, an antioxidant, an antineoplastic agent, an agent affecting the immune response, an antithrombotic, an antihyperlipidemic agent, a cardiac drug, a thyromimetic or antithyroid drug, an adrenergic, an antihypertensive agent, a cholinergic, an anticholinergic, an antispasmodic, an antiulcer agent, a skeletal and/or smooth muscle relaxant, a prostaglandin, a general inhibitor of the allergic response, an antihistamine, a local anesthetic, an analgesic, a narcotic antagonist, an antitussive, a non-steroidal anti-inflammatory agent, a steroidal anti-inflammatory agent, an antioxidant, a vaso-active agent, a bone-active agent, an antiarthritic, a vitamin, or a diagnostic agent.

In certain embodiments, the composition optionally includes one or more of an antimicrobial, an antibiotic, an antimyobacterial, an antifungal, an antiviral, a local anesthetic, an analgesic, an antioxidant, an antiseptic agent, a vitamin, or combinations thereof.

Just to give a few examples, particular antimicrobial compounds that may be useful in the practice of the present invention include, for example, aminoglycosides (e.g., amikacin, gentamicin, tobramycin, and combinations thereof), amoxicillin (with or without clavulanate), amphotericin, ampicillin (with or without sulbactam), azithromycin, aztreonam, bacitracin, cefazolin, cefepime, cefotaxime, cefotetan, cefpodoxime, ceftazidime, ceftizoxime, ceftriaxone, cefuroxime, cephalexin, cephalosporins, chloramphenicol, ciprofloxacin, clarithromycin, clindamycin, clotrimazole, dapsone, dicloxacillin, doxycycline, erythromycin, fluconazole, furazidine (with or without sodium chloride), furazolidone, gatifloxacin, gentamycin, imipenem/cilastatin, isoniazid, itraconazole, kanamycin, ketoconazole, metronizadole, minocycline, nafcillin, neomycin, nitrofural, nitrofuratonin, nystatin, ofloxacin, penicillin, pentamidine, piperacillin, polymyxin, rifampicin, quinupristin, streptomycin, tetracycline, ticarcillin, trimethoprim, vancomycin, etc. Natural antimicrobials such as, for example, propolis, may also be employed. Combinations of such antimicrobial agents may also be employed.

Examples of particular analgesics useful in accordance with the present invention include, for instance, morphine sulfate, codeine sulfate, meperidine, and nalorphine, or combinations thereof.

Examples of particular anesthetics useful in accordance with the present invention include, for instance, procaine, lidocaine, tetracaine and dibucaine, or combinations thereof.

In certain embodiments, the inventive hemostatic compositions include one or more pharmaceutical agents selected from the group consisting of chlorhexidine (an antiseptic), furazidine, propolis, mexidole, dimexide (i.e., DMSO), hydrogen peroxide, saline, epinephrine and combinations thereof.

The amount of additional therapeutic agent present in the compositions of this invention will typically be no more than the amount that would normally be administered in a composition comprising that therapeutic agent as the only active agent. In certain embodiments, the amount of additional therapeutic agent in the inventive compositions will range from about 50% to 100% of the amount normally present in a composition comprising that agent as the only therapeutically active agent.

Uses of the Inventive Hemostatic Compositions

The compositions of the present invention are useful as hemostatic agents. Accordingly, the present composition is useful for controlling, lessening the severity of, or stopping bleeding, for promoting cellular adhesion, or for treatment of an injury such as the site of a wound or accidental injury, an opening incised during a surgical operation, or a puncture site remaining open after removing, for example, a catheter or dialysis needle. Thus, one aspect of the present invention relates to a method for controlling or lessening the severity of bleeding. In some embodiments, the bleeding is associated with a wound or other accidental injury, a dental procedure, or a surgical procedure. Inventive compositions, methods, and devices are useful to treat, for example, dental bleeding, nasal bleeding, bleeding by hemophiliacs, bleeding associated with accidental cuts or abrasions (e.g., as occur in shaving, handling papers, playing games, etc.), wounds, surgical incisions, and other surface bleeding or injury. In other embodiments, the inventive compositions are used in methods of treating arterial bleeding as may be encountered the battlefield, auto accidents, or other incidents of severe trauma. The synergistic hemostatic properties that emerge from the novel components of the invention permit use of the compositions in such methods.

The inventive compositions are also useful in the treatment of burns or other wounds (e.g., necrotic trophic ulcers, diabetic foot syndrome, etc.). Arresting haemorrhage from a wound bed can minimize scar formation or other damage. In some embodiments of the invention, compositions useful for treatment of burns or other wounds (e.g., epinephrine) can included in the inventive compositions. Alternatively or additionally, various antimicrobial and/or antiseptic agents may be included. In some embodiments, one or more of chlorhexidine, furazidine, propolis, mexidole, are included. Particularly useful agents for inclusion in inventive compositions for the treatment of burns include hyaluronic acid, propolis, lidocaine, aloe and/or papaya. In some embodiments, a dressing for minor burns is prepared using a non-woven textile to which a composition is applied, where the composition includes chamomile and nettle components, a biocompatible polymer (e.g., alginate and/or hyaluronic acid), kaolin/chitosan/fibrinogen/thrombin components, and an additional therapeutic agent (e.g., propolis and/or papaya).

Those of ordinary skill in the art will readily appreciate any of a number of other desirable applications or uses for inventive compositions and devices.

Inventive compositions are delivered or applied to a site of bleeding (or other damage) and are maintained in contact with the site, optionally with light pressure (e.g., applied manually or my means of an adhesive or elastic bandage), for a period of time to reduce or eliminate bleeding. As described below in Example 5, compositions of the present invention have been tested in animal models of severe hemorrhage and have been found capable of greatly reducing and even stopping such bleeding in less than 1 minute. In embodiments with lesser injuries (e.g., cuts, abrasions, lacerations and burns), the inventive compositions disclosed herein are able to arresting bleeding in approximately 30 seconds. Thus, according to some embodiments, the invention provides compositions, devices, and methods that stop bleeding in less than a minute. In some embodiments, bleeding is stopped in less than about, 50, 40, 30, 20, or 10 seconds. In some embodiments, bleeding is stopped within 30-40 seconds. In other embodiments, inventive compositions or devices may be kept in contact with a damaged site for several minutes, or hours, or even days, optionally with one or more changes during the period.

It will also be appreciated that compositions of the present invention can be employed in combination therapies. That is, compositions can be administered concurrently with, prior to, or subsequent to, one or more other desired therapeutic agents or medical procedures. The particular combination of therapies (therapeutic agents or procedures) to employ in a combination regimen will take into account compatibility of the desired therapeutic agents and/or procedures and the desired therapeutic effect to be achieved. It will also be appreciated that therapies employed may achieve a desired effect for the same disorder (for example, the present composition may be administered concurrently with another agent used to treat the same disorder), or they may achieve different effects (e.g., control of any adverse effects).

Formulations and Devices Including the Inventive Hemostatic Compositions

As will be appreciated by those of ordinary skill in the art, inventive hemostatic compositions may desirably be incorporated into any of a variety of formulations or devices for topical or transdermal administration.

For example, inventive hemostatic compositions may be formulated as ointments, pastes, creams, lotions, gels, powders, solutions, sprays, or inhalants. In certain embodiments, as discussed above, the hemostatic compositions are incorporated in or on a gel.

Alternatively or additionally, the hemostatic compositions may be applied onto or incorporated within a surface, device, or material that is used to deliver the composition to a wound site. To give but a few non-limiting examples, the compositions may be applied to the surface of a cotton swab or other elongated device for application to a wound, or may be coated on or encased within a flexible surface that can be used to cover, in whole or in part, a wound. In certain embodiments of the invention, the composition is applied to or incorporated into a dressing, such as a bandage or patch, for application to the surface of a wound. In other embodiments, the compositions is applied to or incorporated into biodegradable and/or bioresorbable materials for application within a wound or within a subject (e.g., sutures). Biodegradable and/or bioresorbable, as used herein, describe materials that are degraded in the body of a subject into smaller molecules of a size that allows the particles to be transported by the blood stream or lymph system, or to be absorbed by cells of the body, thereby removing the materials from the site of application. Examples of such materials include polyglycolic acid ("PGA"), copolymers of PGA and polylactic acid ("PLA"), polydioxanone, gelatine, collagen, chitan, alginate, cellulose, carboxymethylcellulose or hydroxymethylcellulose. The hemostatic compositions of the invention may also be presented in the form of a sponge or other porous material.

In general, a dressing according to the present invention will include a material onto which the inventive composition is applied. The composition may be localized to only a portion of the material, or may substantially cover a material surface.

In general, the thickness with which the inventive hemostatic composition is applied to a material will be selected to ensure delivery of an adequate amount of composition to promote the mechanical formation of a clot. In some embodiments of the invention, it is desirable that the composition be applied to a material with a thickness not less than about 0.05, 0.04, 0.03, or 0.02 mm. In some embodiments, the composition is applied with a thickness not less than 0.025 mm. In some embodiments, the composition is applied with a thickness of 0.3 mm.

An inventive dressing may also include an attachment means, such as an adhesive, an elastic bandage, a tie, or other means, allowing the dressing to be secured to the site of a wound. In some embodiments, the dressing will include an adhesive substrate (e.g., a plastic or other flexible material with an adhesive surface) whose adhesive surface is partially covered by a fabric material to which an inventive hemostatic composition has been applied.

Desirable materials onto which inventive compositions are applied include any fabric, textile or other material compatible with the composition and its intended use. In some embodiments, it is desirable to use a gas-permeable material, for example to limit "hothouse" effects underneath a dressing. In some embodiments, it is desirable to employ an absorptive material, for example to remove liquid (particularly aqueous liquids such as blood or water) from a wound site. Such absorptive characteristics may, in some cases, enhance the healing capabilities of inventive dressings, for example by promoting coagulation.

Materials for use in accordance with this aspect of the present invention include woven and non-woven materials. In some embodiments of the invention, non-woven materials are employed. For example, non-woven materials based on cellulose fibers, such as cellulose or viscose cotton, may be employed. In some embodiments, a material comprising viscose fibers is used.

In some embodiments of the invention, particularly those utilizing non-woven materials, the material is stitched with reinforced thread. Such stitching can enhance the stability of the material, and in particular can minimize the risk of material fibers falling into the wound. Rows of stitching may be spaced apart from each other by a distance that is desirably less than about 10 mm. In some embodiments, stitched rows are separated by more than about 1 mm. In other embodiments, stitched rows are separated by about 2, 3, 4, or 5 mm. In some embodiments, stitched rows are separated by 4.0 mm. Often it will be desirable for rows to be evenly spaced. Those of ordinary skill in the art will readily appreciate, however, that irregular spacing is also contemplated by and encompassed within the present invention.

Materials to which inventive compositions are or have been applied may be cut or otherwise formed into any desirable shape. In some embodiments, square, rectangular, circular, or oval-shaped "pads" may be desirable. In other cases, it may be useful to cut or otherwise adjust a device's size to accommodate dimensions of a particular site or wound. Those of ordinary skill in the art will readily appreciate that a wide range of different sizes and shapes of devices is encompassed within the scope of the present invention.

Inventive dressings and other devices may optionally be sterilized and packaged, as is known in the art. For example, sterilization may be accomplished by subjecting a packaged composition or device to radiation, for example gamma radiation or E-beam, or by treatment with ethylene oxide. In some embodiments, inventive compositions or devices are packaged in packaging that is selected and arranged to facilitate removal of a sterile composition or device without contamination. In some embodiments, the packaging is waterproof, for example comprising aluminum foil, plastic, or other conventional material that is easily sterilized. In other embodiments, the packaging is not waterproof, for example comprising paper.

The dressings and bandage comprising the inventive compositions are sufficiently malleable to be flattened out and packaged. In certain embodiments, however, any residual stiffness can be reduced by the additional of glycerol at amounts known to those of skill in the art.

EXAMPLES

Example 1

Preparation of an Inventive Hemostatic Composition

The present Example describes preparation of an exemplary hemostatic composition according to the present invention.

Chamomile/Nettle/Alginate Component Preparation 3.55 g of pharmaceutical chamomile flowers and 1.3 g of dioecious nettle leaves were ground in a mill to a powdery consistency. 200 ml of hot, distilled water was poured over the mixture, and it is boiled for 15 minutes. The mixture was then cooled to a temperature of 40° C. and filtered. The volume of the herbal extract thus obtained was then reduced to 200 ml. 8.3 g of an alginate of sodium was added, and the mixture was maintained at room temperature for 12 hours, with occasional stirring.

The chamomile/nettle/alginate composition was layered onto a textile material to form a first composite bandage comprising chamomile/nettle and biocompatible polymer. The chamomile/nettle/alginate composition was evenly applied onto a nonwoven material made of a combination of viscose cotton fibers stiched with reinforcing thread in rows spaced in 4 mm intervals. Approximately 120 grams of the composition was applied per square meter. The resulting layered textile was air-dried, and cut into pads of varying sizes.

Kaolin/Chitosan/Fibrinogen/Thrombin Component Preparation

A fibrinogen buffer was prepared according to the following formula:

| | |
|---|---|
| 100 mM TRIS Buffer | 16.76 g |
| 10 mM NaCl | 2.94 g |
| 1.5% Sucrose | 15 g |
| 80 mg/g FBS | 16 g |
| 15 mg/g Tween | 3.0 g |

Each of the above materials was dissolved in 100 ml of 1% PBS. Twenty-five grams of fibrinogen was mixed into the buffer at room temperature for 40-60 minutes, and the resulting solution was refrigerated at 4° C. The solution proved stable for up to two weeks.

A thrombin buffer was prepared according to the following formula:

| | |
|---|---|
| 150 mM NaCl | 8.72 g |
| 10 mM TRIS | 1.58 g |
| 40 mM CaCl | 4.44 g |
| 100 mM LLysine | 18.76 g |
| 100 mg/g FBS | 18.76 g |

Each of the above materials was dissolved in 100 ml of 1% PBS. Approximately 1000 kilo units ("KU") of thrombin was added to the buffer and dissolved at room temperature for 20 minutes. The solution was then refrigerated at 4° C., and was stable for up to two weeks.

Ten grams of kaolin was dissolved in 200 ml of PBS by mixing at room temperature for 15 minutes. The solution was observed to ensure that the kaolin did not settle. Approximately 2-5 grams of the kaolin solution was added to each first composite bandage of approximately 7 inches by 9 inches.

Ten grams of chitosan was dissolved in 200 ml of PBS. The pH was acidified to less than 6.5 by addition of hydrochloric acid. The mixture was then heated to 70° C. and mixed. After 40 minutes of mixing, the pH was adjusted to 7.4 by addition of sodium hydroxide. The solution was then cooled.

The kaolin/chitosan/fibrinogen/thrombin components were added to each first composite bandage as follows. First, the bandages were placed in a plastic pan and 2 grams of kaolin solution prepared above was added to each bandage. Next, 4 grams of the chitosan solution was added to each bandage. The bandages were then frozen at minus 80° C. for 15 minutes. Ten grams of the fibrinogen buffer prepared above was applied to each bandage, and the bandages were again frozen at minus 80° C. for 15 minutes. The thrombin buffer prepared above was then applied such that 100 KU was added to each bandage. The resulting second composite bandages were frozen at minus 80° C. freezer for 45 minutes. Prior to freezing, the bandages were wrapped in a half-circle or folded-over after application of the fibrinogen and thrombin so that they would fit inside lyophilizer bottles.

After 45 minutes, the second composite bandages were checked to ensure that they were frozen. Any unfrozen bandages were briefly placed in liquid nitrogen to ensure proper lyophilization. The bandages were lyophilized for 12-18 hours. At the end of the lyophilization process, the bandages were sufficiently malleable to be flattened out and packaged.

Example 2

Preparation of an Inventive Hemostatic Composition

First composite bandages with a chamomile/nettle/biopolymer base were prepared as in Example 1.

A fibrinogen solution was prepared by dissolving 25 grams of fibrinogen in 1% PBS at 37° C. for 60 minutes with vigorous agitation every 15 minutes. It was observed that not all of the fibrinogen entered solution.

A thrombin solution was prepared by dissolving approximately 1000 KU of thrombin in 100 ml PBS to which had been added 2.5 grams glycine and 5.0 grams glucose.

The first composite bandages were placed in a plastic pan and 2 grams of the kaolin solution as prepared above was added to each bandage. Subsequently, 4 grams of the chitosan solution prepared above was applied to each bandage. The bandages were frozen at minus 80° C. for 15 minutes.

Ten grams of the fibrinogen solution was applied, and the bandages were again placed frozen at minus 80° C. for 15 minutes. A suitable volume of the thrombin solution prepared above was added such that approximately 100 KU of thrombin was added per bandage. The bandages were wrapped in a half-circle or folded-over after application of the fibrinogen and thrombin so they would fit inside the lyophilizer bottles. The resulting second composition bandages were frozen at 80° C. for 45 minutes.

After 45 minutes, the bandages were checked to ensure freezing. If the bandages were not frozen by 45 minutes after the thrombin application, the bandages were dipped in liquid nitrogen before lyophilization. The bandages were lyophilized or 12-18 hours. Following lyophilization, the bandages were malleable and able to be flattened-out and packaged.

Example 3

Preparation of an Inventive Hemostatic Composition

First composite bandages with a chamomile/nettle/biopolymer base were prepared as in Example 1.

A fibrinogen buffer was prepared by dissolving the following components in 100 ml of 1% PBS:

| 100 mM TRIS Buffer | 16.76 g |
| 10 mM NaCl | 2.94 g |
| 1.5% Sucrose | 15 g |
| 80 mg/g Human Serum | 16 g |
| 15 mg/g Tween | 3.0 g |

Twenty-five grams of human fibrinogen was mixed into the buffer at room temperature for 40-60 minutes. The resulting solution was stored at 4° C. and was stable for up to two weeks.

A thrombin buffer was prepared by dissolving the following components in 100 ml of 1% PBS:

| 150 mM NaCl | 8.72 g |
| 10 mM TRIS | 1.58 g |
| 40 mM CaCl | 4.44 g |
| 100 mM L-Lysine | 18.76 g |
| 100 mg/g Human Serum | 18.76 g |

Approximately 1000 KU of human thrombin was added to the thrombin buffer and dissolved at room temperature for 20 minutes. The resulting solution was stored at 4° C. and was stable for up to two weeks.

Kaolin was prepared by dissolving 10 grams in 200 ml of PBS, followed by mixing at room temperature for 15 minutes. The mixture was not permitted to settle.

Chitosan was prepared by dissolving 20 grams in 400 ml of PBS. The solution was acidified to a pH of less than 6.5 by addition of hydrochloric acid. The solution was then heated to 70° C. and mixed. After 40 minutes, the pH was raised to 7.4 by addition of sodium hydroxide. The solution was then allowed to cool.

The first composite bandages were placed in a plastic pan. Two to four grams of the kaolin solution prepared above were applied to each bandage. Four to ten grams of the chitosan solution were then applied to each bandage. The bandages were then frozen at minus 80° C. for 15 minutes.

Ten to twenty grams of the fibrinogen solution was added to each bandage, followed by the addition of a suitable volume of thrombin buffer such that 100-200 KU of thrombin was added to each bandage. The resulting second composite bandages were wrapped in a half circle or folded over after fibrinogen and thrombin application so that they would fit inside lyophilizer bottles. The bandages were then frozen at minus 80° C. for 45 minutes.

After 45 minutes, the bandages were checked to ensure adequate freezing. If the bandages were not frozen by 45 minutes after thrombin application, they were dipped in liquid nitrogen before lyophilization. The bandages were lyophilized for 12-18 hours. After lyophilization, the bandages were malleable and able to be flattened out and packaged.

Example 4

Preparation of an Inventive Hemostatic Composition

First composite bandages with a chamomile/nettle/biopolymer base were prepared as in Example 1.

Fibrinogen was prepared by dissolving 25-50 grams of human fibrinogen in 1% PBS at 37° C. for 60 minutes with vigorous agitation very 15 minutes. It was observed that not all the fibrinogen entered solution.

Thrombin was prepared by dissolving approximately 1000-2000 KU in 100 ml of PBS to which had been added 2.5 grams of glycine and 5 grams of glucose.

The first composite bandages were placed in a plastic pan and 2-5 grams of the kaolin solution prepared above was applied. Four to ten grams of the kitosan solution was then applied, and the bandages were frozen at minus 80° C. for 15 minutes.

Ten to twenty grams of the fibrinogen solution prepared above was applied to each bandage. The bandages were again frozen at minus 80° C. for 15 minutes. Thrombin was then applied by adding an appropriate volume of the thrombin solution prepared above such that approximately 100-200 KU was applied per bandage. The resulting second composite bandages were wrapped in a half-circle or folded-over after fibrinogen and thrombin application so that they would fit inside lyophilizer bottles. The bandages were then frozen at minus 80° C. for 45 minutes.

After 45 minutes, the bandages were checked to ensure freezing. If the bandages were not frozen by 45 minutes after thrombin application, they were dipped in liquid nitrogen before lyophilization. The bandages were lyophilized for 12-18 hours. Following lyophilization, the bandages were malleable and able to be flattened out and packaged.

Example 5

Animal Studies

Inventive hemostatic composition bandages prepared as above are used in the following experiments to evaluate the hemostatic qualities. Various parameters evaluated include survival, hemostatic efficacy, temperature elevation (and tissue damage) when applied to a swine model of uncontrolled hemorrhagic groin injury, temperature elevation (and tissue damage) when applied applied to a swine model of uncontrolled hemorrhage liver and splenic injuries. In particular experiments, the injury is inflicted using a captive bolt gun firing a .25 caliber round at close range, which replicates a large caliber gunshot wound at medium range. Therefore, the effects of blast damage on tissue, vasculature and bone afford a more clinically relevant scenario in which the performance of the bandages/dressing prepared above can be assessed.

Materials and Methods

It is known by those of skill in the art that swine or pigs are anatomically similar to humans and are excellent models to assess the efficacy of treatments for traumatic injuries in humans. The experiments reported herein are conducted according to the principles set forth in the Guide for the Care and Use of Laboratory Animals (Institute of Laboratory Animals Resources, National Research Council, and National Academy Press, 1996.

Yorkshire swine (30-40 kg, Animal Biotech Industries, Danboro, Pa.) are fed until the night before experiment with free access to water. Anesthesia is induced with intramuscular injection of ketamine hydrochloride (HCL) (30 mg/kg) and inhalation of 3% isofluorone. After placement of endotracheal tube, the isoflurane concentration is reduced to 2.2% until initiation of injury. After the onset of bleeding, the level is reduced to 1% to 1.5% and then regulated to maintain sedation thereafter. The animals are allowed to breathe spontaneously using a mixture of oxygen and air administered through a Narkomed M ventilator (North American Dräger, Telford, Pa.). End tidal $CO_2$ and respiration rate are continuously monitored and regulated between 34 and 45 mm Hg, and are intermittently recorded. Rectal temperature is monitored and maintained between 36.0 and 37.8° C. using a Bear Hugger device (Model 505, Bair Hugger, Minn.). An 18 gauge angiocatheter is placed in the right carotid artery and connected to the arterial line to acquire blood pressure and withdraw blood samples. The external jugular vein is then cannulated with a 22 gauge angiocatheter and 9 Fr introducer to place a 7.5 Fr oximetric thermodilution pulmonary artery catheter (Schein Care Corp., Irvine, Calif.). The catheter is attached to a hemodynamic monitoring system (Hewlett Packard, Palo Alto, Calif.) to allow for continuous monitoring of the mean pulmonary artery pressure (MPAP). Resuscitation fluid is infused through this venous access. The goal of resuscitation is to return to baseline MPAP or mean arterial pressure ("MAP"). All catheters are flushed with a citrated flush solution (50 mL of acid-citrate-dextrose in 500 mL of 0.9% saline solution) to maintain patency. Tissue oxygenation is measured using near infrared spectroscopy (Inspectra-hutchinson technologies, MN) with the probe applied to the lower extremity.

Products

The standard gauze dressing consisted of thick 8×10 inch absorbent gauze pad with elastic bandage (Cinch Tight, H&H Associate, Bena, Va.). Bandages comprising the hemostatic composition of the invention were prepared as described in Examples 1 through 4. All products require standard dressing with application of manual pressure on the dressing.

Injury—Groin

After a brief period of stabilization, the groin area is exposed and abductor and quadriceps muscles exposed in the proximal medial right thigh through a surgical incision. Injury is induced by transecting the femoral blood vessels to produce uncontrolled hemorrhage as described by Alam et al, 2004, *Application of a zeolite hemostatic agent achieves 100% survival in a lethal model of complex groin injury in Swine*, J Trauma 56, 974-83. This injury involves cutting the superficial and deep femoral vasculature in the groin area. Surgical exposure of the femoral arteries and veins is deliberately avoided to prevent any vessel constriction. At time 0 (onset of injury), a full transection of the superficial and deep femoral arteries and veins is made using a #22 scalpel blade. Blood is collected by suction into a vacuum bowl; aspiration is directed toward the blood accumulating in the groin cavity and not directly at the site of injury.

A second groin injury model is used as follows. After a brief period of stabilization, the groin area is exposed and abductor and quadriceps muscles exposed in the proximal medial right thigh through a surgical incision. Injury is induced by shooting the animal with a captive bolt gun firing a .25 caliber round from a distance on 2-6 inches (QC cattle supplies). Blood is collected by suction into a vacuum bowl; aspiration was directed toward the blood accumulating in the groin cavity and not directly at the site of injury.

Treatment is administered and assessed as follows. After 30 seconds of free bleeding (simulating the response time for arrival of the first responder), the animals (n=30) are randomly assigned to treatment regimen in a blinded fashion and evenly distributed among three treatment groups (n=10 per group): (1) No treatment (NONE); (2) standard dressing (SD); (3) inventive hemostatic composition bandages of the invention. Before application of hemostatic agents, excess blood is evacuated from the wound without disturbing the vascular injury site. This volume is determined and designated as pre-treatment blood loss. During application of hemostatic agents, the dressings are placed to best follow the contours of the wound. Immediately afterward, the wound is packed with standard dressing and manual compression pressure (approximately 150 mm Hg) is applied for 5 minutes, monitored by a pediatric lightly inflated cuff (Soft-Cuff, GE) placed in the standard dressing and recorded with a handheld digital manometer (HM28, Dwyer, MI City, Ind.). At 8 minutes, manual pressure is released and the wound will be closed for the entire length of the experiment (4 hours) by clamping the skin flaps together. At 15 minutes after onset of hemorrhage, a bolus volume of intravenous resuscitation with lactated ringers 500 mL is given through the jugular catheter during a span of 30 minutes using a Masterflex pump (Cole Parmer, Vernon Hills, Ill.) corresponding to a delivery rate of approximately 15 mL/min. The volume of solution required to return MAP to baseline is monitored. Animals are monitored until death or for a total of 2 hours, whichever comes first, and euthanized by injection (100 mg/kg) of Euthasol solution if necessary. The animals are then de-instrumented and the dressings removed and weighted. The weight of the dressings normalized to their weight prior to use in the animal is designated as post-treatment blood loss.

Injury—Liver

The liver is the most commonly injured abdominal organ causing hemorrhagic death. Grade V hepatic injuries, as classified by the Liver Injury Scale of the American Association for the Surgery of Trauma, involve extensive parenchymal damage combined with major vascular laceration. The reported mortality rates for these injuries exceeds 60%. A liver injury model is established as follows. Once the swine are anesthetized, left cervical cut-downs are performed and polyethylene catheters are inserted into the common carotid artery and the external jugular vein. The arterial catheter is used for continuous monitoring and blood sampling. Mean arterial pressure (MAP), systolic blood pressure (SBP), diastolic blood pressure (DBP), and heart rate (HR) are continuously recorded and averaged every 10 seconds using a digital data collection system with a blood pressure analyzer (DigiMed, Louisville, Ky.). The venous line is used for administration of the resuscitation fluids.

The animals undergo a midline celiotomy, suprapubic Foley catheter placement. After a 15-minute stabilization period, the towel clamps are removed and the abdomen is dried. Pre-weighed laparotomy pads are placed in both paracolic gutters and the pelvis to facilitate blood collection. A standardized grade V liver injury (injury to a central hepatic vein) is created with a specially designed clamp (see Moore, et al., 1995, *Organ injury scaling*, Surg Clin North Am 75, 293-303). The clamp is positioned in the middle of the liver, placing the right hepatic vein, the left hepatic vein, and the portal vein at risk for injury. This protocol is based upon experience in previous studies of uncontrolled hemorrhagic shock using the grade V liver injury model (see Holcomb, J. B., 1999, *Effect of dry fibrin sealant dressings versus gauze packing on blood loss in grade V liver injuries in resuscitated swine*. J Trauma 46, 49-57; Schreiber, M. A. et al., 2003, *The effect of recombinant factor VIIa on non-coagulopathic pigs with grade V liver injuries*, J Am Coll Surg 196, 691-7). The time of injury is considered the start time of the 30-second injury period.

Resuscitation is delayed for 30 seconds to simulate a realistic combat situation. After 30 seconds of uncontrolled hemorrhage, the initial blood loss, measured by wall suction, and the preweighed laparotomy pads is determined.

The injury model is repeated as follows to assess the inventive hemostatic compositions disclosed herein. Once the swine are anesthetized, a left cervical cutdown is performed and polyethylene catheters are inserted into the common carotid artery and the external jugular vein. The arterial catheter is used for continuous monitoring and blood sampling. Mean arterial pressure (MAP), systolic blood pressure (SBP), diastolic blood pressure (DBP), and heart rate (HR) are continuously recorded and averaged every 10 seconds using a digital data collection system with a blood pressure analyzer (DigiMed, Louisville, Ky.). The venous line is used for administration of the resuscitation fluids. The animals undergo a midline celiotomy, suprapubic Foley catheter placement.

After a 15-minute stabilization period, the towel clamps are removed and the abdomen dried. Preweighed laparotomy pads are placed in both paracolic gutters and the pelvis to facilitate blood collection. A grade V liver injury is created by shooting the animal with a cattle stunner firing a .25 caliber round from a distance on 2-6 inches (QC cattle supplies) positioned in the middle of the liver, placing the right hepatic vein, the left hepatic vein, and the portal vein at risk for injury. Blood is collected by suction into a vacuum bowl; aspiration is directed toward the blood accumulating in the abdominal cavity and not directly at the site of injury.

Treatment is assessed as follows. After 30 seconds of free bleeding (simulating the response time for arrival of the first responder), the animals (n=30) are randomly assigned to treatment regimen in a blinded fashion and evenly distributed among three treatment groups (n=10 per group): (1) no treatment (NONE); (2) standard dressing (SD); (3) bandages comprised of compositions of the invention. Before application of hemostatic agents, excess blood is evacuated from the wound without disturbing the vascular injury site. During application of hemostatic agents, the dressings are placed to best follow the contours of the wound. Immediately afterward, the wound is packed with standard dressing and manual compression pressure (approximately 150 mm Hg) are applied for 5 minutes, monitored by a pediatric lightly inflated cuff (SoftCuff, GE) placed in the standard dressing and recorded with a handheld digital manometer (HM28, Dwyer, MI City, Ind.). At 8 minutes, manual pressure is released and the wound is closed for the entire length of the experiment (4 hours) by clamping the skin flaps together. At 15 minutes after onset of hemorrhage, a bolus volume of intravenous resuscitation with lactated ringers 500 mL is given through the jugular catheter during a span of 30 minutes using a Masterflex pump (Cole Parmer, Vernon Hills, Ill.) corresponding to a delivery rate of approximately 15 mL/min. The volume of solution required to return MAP to baseline is monitored. Animals are monitored for a total of 1 hour then euthanized by injection (100 mg/kg) of Euthasol solution. The animal is then de-instrumented and the dressings removed and weighted. The weight of the dressings normalized to their weight prior to use in the animal is designated as post-treatment blood loss.

Data

The following data are collected during each experiment to allow direct comparison of the hemostatic compositions of the invention to "no treatment" and standard dressing control groups:

Pre-injury mean arterial pressure (MAP), which is a term used in medicine to describe a notional average blood pressure in an individual, and is defined as the average arterial pressure during a single cardiac cycle;

Post-injury mean arterial pressure (MAP);

Blood loss in milliliters (ml) after 30 seconds of bleeding post injury;

Median Blood loss after treatment in milliliters (ml);

Median fluid resuscitation after injury—the swine will be resuscitated with lactated ringers solution (LR) thirty seconds after the initiation of hemorrhage to achieve and maintain the baseline MAP throughout the duration of the study;

Hematocrit at injury—hematocrit or packed cell volume (PCV) or erythrocyte volume fraction (EVF) is the proportion of blood volume that is occupied by red blood cells;

Hematocrit after treatment;

Dressing failure—this parameter indicates that the dressing applied has been unsuccessful in stemming the profuse bleeding encountered after vascular laceration or vascular transaction.

Success is determined by the cessation of bleeding after injury by manual compression with the compositions of the invention. The above-mentioned data points are used to compare the test groups and type of injury.

Results

Figure 1:
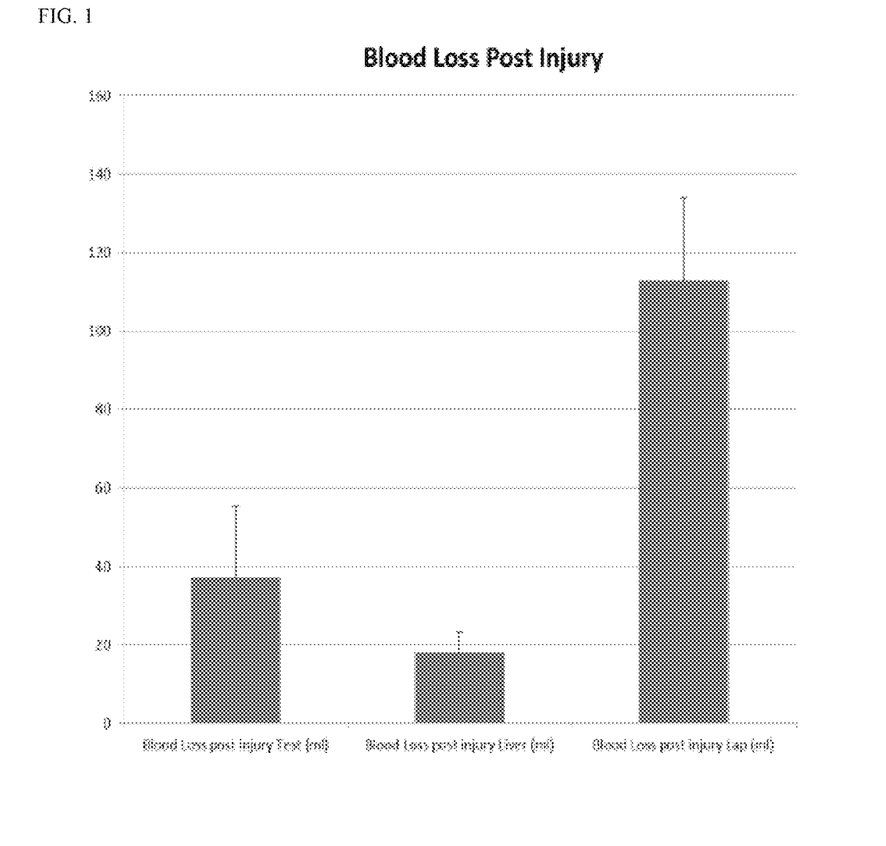
FIG. 1 is a bar graph showing post-injury blood loss after application of a bandage comprising the experimental compositions disclosed herein to a groin injury swine model after 1 minute of hemorrhage ("Test"; left) and to a liver injury swine model after 1 minute of hemorrhage (middle) as compared to application of a standard laparotomy (lap) pad to a groin injury animal model after 1 minute of hemorrhage (right).

Several sets of experiments were conducted as outlined above. In both liver and groin injury models, the bandages demonstrated excellent adherence strength; adhering the injured area for over an hour, even under vigorous shaking. This adherence was facilitated through the pliancy of the bandages according to embodiments of the invention, and was a significant improvement of current traumatic injury hemostatic dressings. Moreover, the bandages achieved hemostasis and completely stopped bleeding from a grade 5 liver injury that included near total removal of the left lobe of the liver. (FIG. 1; middle). Such results were maintained for over 1 hour. The bandages also stopped bleeding for over 1 hour in a groin injury model despite vigorous manipulation. These results clearly indicated successful application of the hemostatic compositions of the invention. In several instances, pressure was applied for 3-5 minutes, which increased effectiveness of the bandages.

Figure 2:
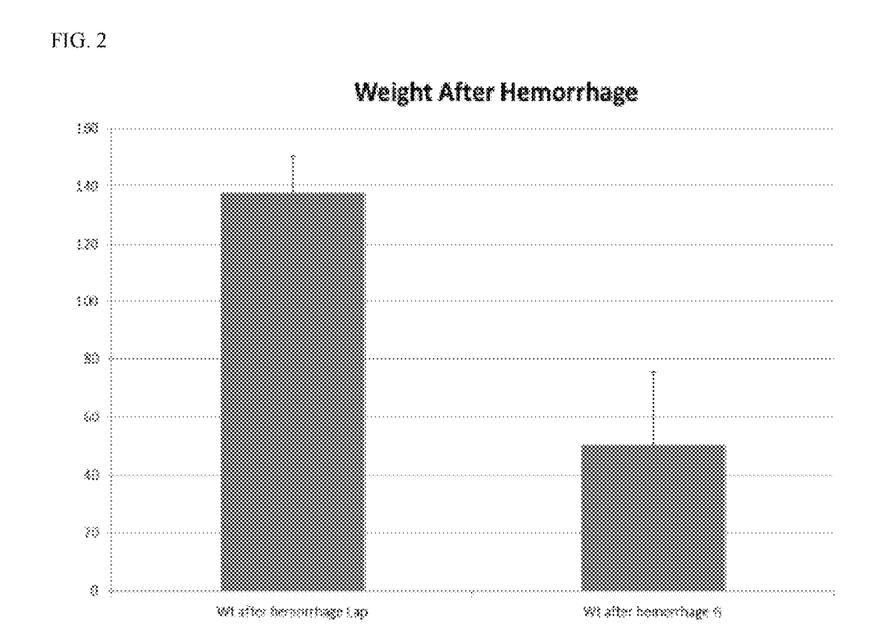
FIG. 2 is a bar graph showing the weight of a standard laparotomy pad (left) after it was extracted from the wound cavity in a swine model of profuse hemorrhage; the weight of the pad indicated that it was ineffective at controlling profuse hemorrhage. The weight of the standard laparotomy pad was compared to the weight of a bandage comprising the experimental compositions disclosed herein (right) after it was extracted from the wound cavity in the same animal model of profuse hemorrhage; the weight of the pad indicated that it was effective at controlling profuse hemorrhage.
Figure 3:
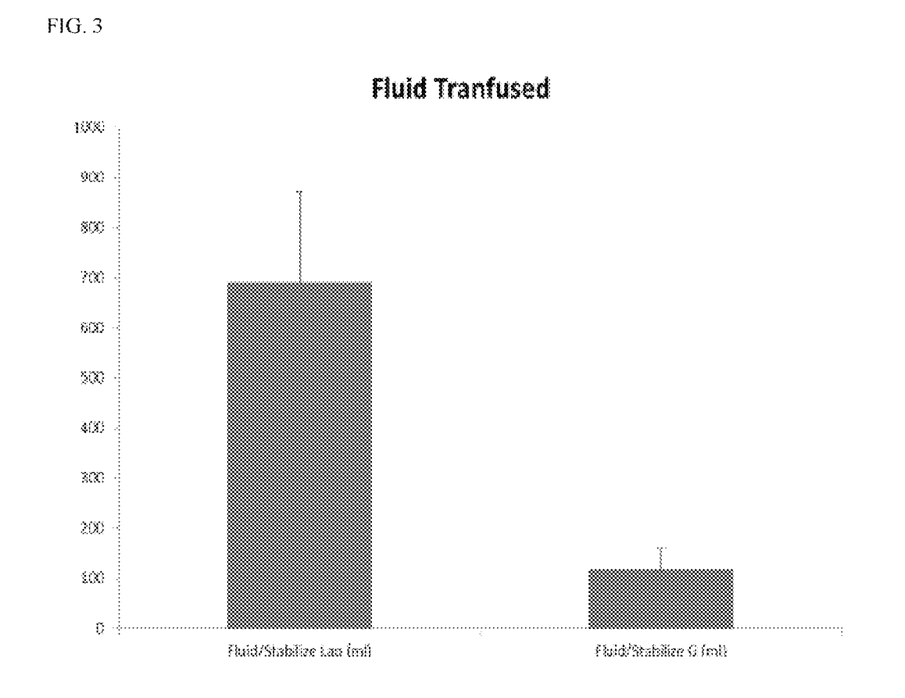
FIG. 3 is a bar graph showing the median amount of lacted ringers solution required to stabilize/resuscitate a swine model of groin injury after one minute of hemorrhage. The amount of fluid required after application of a standard laparotomy pad (left) is compared to the amount of fluid required after application of a bandage comprising the experimental compositions disclosed herein (right).

There were no statistically significant differences among treatment groups in animal body weight, estimated blood volume, sex distribution, baseline MAP, pre-injury MAP, pretreatment blood loss, or baseline hematocrit at injury. Post-treatment blood loss was dramatically reduced in the groups treated with the inventive hemostatic compositions disclosed herein. (FIGS. 1 and 2). In general, compared to gauze treatment, post-treatment blood loss was reduced by a factor of 4-10 or more (i.e., at least 40-90%) with respect to both total blood loss and blood loss in ml per kg of body weight when the inventive compositions were applied. Resuscitation fluid use was also greatly reduced in the inventive hemostatic composition groups. (FIG. 3). Survival percentages for groups treated with the inventive composition was almost 100%, compared to zero and 25% for the "no treatment" and gauze-treated groups, respectively. Hemostasis was observed at 2 minutes or less in every animal treated with the inventive compositions, compared with no observation of hemostasis in the untreated and gauze-treated groups. In a significant majority of animals treated with bandages comprising the inventive compositions, hemostasis was observed in less than 1 minute, with a number of animals exhibiting hemostasis within about 30 seconds. Dressing failure was not observed in bandages comprised of the inventive compositions.

CONCLUSION

Inventive compositions, bandages, dressings, etc. disclosed in the present application demonstrate unsurpassed hemostatic abilities relative to untreated and standard gauze-treated controls. Specifically, subjects treated with the inventive bandages exhibit a post-injury MAP closer to their respective pre-injury MAP, have significantly reduced blood loss post-treatment when normalized to pre-treatment blood loss, demonstrate lower median fluid resuscitation, and exhibit almost no dressing failure. Hemostatis is initiated almost immediately, and a complete hemostatis is attained within 1 to 2 minutes in the majority of subjects and can be completely maintained through the duration of the experiments In fact, the inventive bandages disclosed herein staunch bleeding entirely as long as contact is maintained with the wound, and a nearly 100% survival rate is observed during the duration of the experiments. The studies indicate that hemostatic bandages according to embodiments of the invention have unmatched ability to arrest bleeding that occurs in severe wounds, thereby permitting patients to be safely evacuated from the field to a trauma center where the extent of his injuries can be evaluated and treated. The protocols above accurate replicate the type of injury sustained in a combat situation with the patient having sustained single or multiple gunshots, in the extremity and the abdomen.

EQUIVALENTS

Those of ordinary skill in the art will appreciate that the foregoing has described certain preferred embodiments of the invention. Various modifications, changes, and substitutions to compounds, materials, or methods described herein may be made without departing from the spirit or scope of the present invention, whose boundaries are established only by the subject matter of the appended claims.

We claim:

1. A hemostatic composition comprising therapeutically effective amounts of chamomile, dioecious nettle, kaolin, chitosan, fibrinogen, thrombin and a biocompatible polymer, wherein the kaolin:biocompatible polymer ratio by weight is 0.01-0.03:1, the chitosan:biocompatible polymer ratio by weight is 0.02-0.07:1, the fibrinogen:biocompatible polymer ratio by weight is 0.30-1.2:1, and the thrombin:biocompatible polymer ratio by weight is 0.03-0.08:1.

2. The hemostatic composition of claim 1, wherein the chamomile and dioecious nettle components are present at a weight ratio relative to the biocompatible polymer of 0.3-0.9:1, the kaolin:biocompatible polymer ratio by weight is 0.01-0.03:1, the chitosan:biocompatible polymer ratio by weight is 0.02-0.07:1, the fibrinogen:biocompatible polymer ratio by weight is 0.30-1.2:1, and the thrombin:biocompatible polymer ratio by weight is 0.03-0.08:1.

3. The hemostatic composition of claim 1, wherein the chamomile and nettle components are present at an amount within a weight ratio range of about 0.3-0.9:1 relative to the amount by weight of biocompatible polymer, kaolin is present in a total amount of about 1 to 5 grams, chitosan is present in a total amount of about 4-10 grams, fibrinogen is present in a total amount of about 10 to 20 grams, and thrombin is present at a level of about 100 to 200 kilo units.

4. The hemostatic composition of claim 3, wherein the chamomile and nettle components are present at an amount within a weight ratio range of about 0.3-0.9:1 relative to the amount by weight of biocompatible polymer, chitosan is present in a total amount of about 4 grams, kaolin is present at a total amount of about 1 gram, fibrinogen is present at a total amount of about 20 grams, and thrombin is present at a level of 150 kilo units.

5. The composition according to claim 1, wherein the biocompatible polymer is selected from the group consisting of one or more of agarose, agar, carrageen, alginic acid, alginate, an alginic acid derivative, a hyaluronate derivative, a polyanionic polysaccharide, chitin, chitosan, fibrin, a polyglycolide, a polylactide, a polycaprolactone, a dextran or copolymer thereof, polyvinyl pyrrolidone, a polyacrylate, a wax, a polyethylene-polyoxypropylene-block polymer, wool fat, poly(L-lactic acid), poly(DL-Lactic acid) copoly(lactic/glycolic acid), cellulose, a cellulose derivative, a glycol, polylactide-polyglycolide, polymethyldisiloxane, polycaprolactone, polylactic acid, and ethylene vinyl acetate.

6. The composition according to claim 1, wherein the biocompatible polymer comprises a hydrophilic polymer.

7. The composition according to claim 1, wherein the biocompatible polymer comprises alginic acid, alginate or other alginic acid derivative.

8. The composition according to claim 1, wherein the biocompatible polymer comprises a hydrogel.

9. The composition of claim 1, further comprising an additional therapeutic agent.

10. The composition according to claim 9, wherein the additional therapeutic agent is selected from the group consisting of one or more of an antimicrobial, an antibiotic, an antimyobacterial, an antifungal, an antiviral, a neoplastic agent, an agent affecting the immune response, an antithrombotic, an antihyperlipidemic agent, a cardiac drug, a thyromimetic or antithyroid drug, an adrenergic, an antihypertensive agent, a cholinergic, an anticholinergic, an antispasmodic, an antiulcer agent, a skeletal and/or smooth muscle relaxant, a prostaglandin, a general inhibitor of the allergic response, an antihistamine, a local anesthetic, an analgesic, a narcotic antagonist, an antitussive, a non-steroidal anti-inflammatory agent, a steroidal anti-inflammatory agent, an antioxidant, a vaso-active agent, a bone-active agent, an antiarthritic, a vitamin, and a diagnostic agent.

11. A dressing for topical or transdermal administration comprising the composition of claim 1.

12. The dressing according to claim 11, wherein the dressing comprises a textile material and the composition is applied on one surface of the textile material.

13. The dressing according to claim 11, wherein the textile material comprises a woven or non-woven material.

14. The dressing according to claim 13, wherein the textile material has been stitched with reinforced threads.

15. The dressing according to claim 14, wherein rows of stitching are separated from one another by a distance within the range of 1.0-10.0 mm.

16. The dressing according to claim 12, wherein the textile material is a 6×10 cm pad or a 10×18 cm pad.

17. A method of controlling or lessening the severity of bleeding in a patient in need thereof, wherein said method comprises administering to the site of the bleeding on said patient a composition according to claim 1.

18. A method of controlling or lessening the severity of bleeding in a patient in need thereof, wherein said method comprises the application of the dressing according to claim 11 to the site of the bleeding on said patient.

19. The method according to claim 18, further comprising the application of external pressure.

20. The method according to claim 17, wherein said bleeding is associated with a wound, accidental injury, a dental procedure, or a surgical procedure.

21. The method according to claim 18, wherein the bleeding is arterial bleeding.

22. A method of promoting wound healing in a patient in need thereof, wherein said method comprises applying a composition according to claim 1 to a wound on the patient.

23. A method of treating a burn in a patient in need thereof, wherein said method comprises applying a composition according to claim 1 to a burn on the patient.

24. The method according to claim 17, wherein the bleeding is arterial bleeding.

25. A hemostatic composition comprising a therapeutically effective amount of components including chamomile, dioecious nettle, kaolin, chitosan, fibrinogen, thrombin and a biocompatible polymer in relative amounts as achieved by:
preparing chamomile and dioecious nettle components at a weight ratio relative to the biocompatible polymer of 0.3-0.9:1; and
combining 2-5 g of an about 5% (w/w) solution of kaolin, such that the kaolin:biocompatible polymer ratio by weight is 0.01-0.03:1, 4-10 g of an about 5% (w/w) solution of chitosan, 10-20 g of an about 14% (w/w) solution of fibrinogen and 100-200 KU of thrombin.

* * * * *